United States Patent
Ollila et al.

(10) Patent No.: US 10,857,384 B2
(45) Date of Patent: *Dec. 8, 2020

(54) CONTROLLING AND SHAPING THE DOSE DISTRIBUTION OUTSIDE TREATMENT TARGETS IN EXTERNAL-BEAM RADIATION TREATMENTS

(71) Applicant: Varian Medical Systems International AG, Steinhausen (CH)

(72) Inventors: Santtu Ollila, Helsinki (FI); Mikko Vainio, Espoo (FI); Jarkko Peltola, Tuusula (FI); Janne Nord, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 67 days.

This patent is subject to a terminal disclaimer.

(21) Appl. No.: 16/163,065

(22) Filed: Oct. 17, 2018

(65) Prior Publication Data
US 2019/0046815 A1    Feb. 14, 2019

Related U.S. Application Data

(63) Continuation of application No. 15/273,373, filed on Sep. 22, 2016, now Pat. No. 10,143,859.

(51) Int. Cl.
*A61N 5/10*    (2006.01)

(52) U.S. Cl.
CPC .......... *A61N 5/1031* (2013.01); *A61N 5/1036* (2013.01)

(58) Field of Classification Search
CPC .......... A61N 5/00; A61N 5/10; A61N 5/1077; A61N 5/1048; A61N 5/1036; A61N 5/1031

USPC .......................................................... 378/65
See application file for complete search history.

(56) References Cited

U.S. PATENT DOCUMENTS 10,143,859 B2 * 12/2018 Ollila .................. A61N 5/1031
2018/0078792 A1   3/2018 Ollila et al.

FOREIGN PATENT DOCUMENTS

| CN | 1926552 A | 3/2007 |
|----|-----------|--------|
| CN | 102264435 A | 11/2011 |
| CN | 104815392 A | 8/2015 |
| CN | 105930636 A | 9/2016 |

(Continued)

OTHER PUBLICATIONS

U.S. Appl. No. 15/273,373, Notice of Allowance dated Jul. 26, 2018, 9 pages.

(Continued)

*Primary Examiner* — Jurie Yun
(74) *Attorney, Agent, or Firm* — Kilpatrick Townsend & Stockton LLP

(57) ABSTRACT

Streamlined and partially automated methods of setting normal tissue objectives in radiation treatment planning are provided. These methods may be applied to multiple-target cases as well as single-target cases. The methods can impose one or more target-specific dose falloff constraints around each target, taking into account geometric characteristics of each target such as target volume and shape. In some embodiments, methods can also take into account a planner's preferences for target dose homogeneity. In some embodiments, methods can generate additional dose falloff constraints in locations between two targets where dose bridging is likely to occur.

20 Claims, 15 Drawing Sheets

(56) References Cited

FOREIGN PATENT DOCUMENTS

WO    2014181204    11/2014
WO    2015090459    6/2015

OTHER PUBLICATIONS

Chang et al., Dose Optimization Via Index-Dose Gradient Minimization, Medical Physics, vol. 29, No. 6, Jun. 2002, pp. 1130-1146.
Li et al., A Method to Improve Dose Gradient for Robotic Radiosurgery, Journal of Applied Clinical Medical Physics, vol. 16, No. 6, Nov. 1, 2015, pp. 333-339.
International Application No. PCT/EP2017/073652, International Search Report and Written Opinion dated Dec. 12, 2017, 12 pages.
Schlaefer et al., Stepwise Multi-Criteria Optimization for Robotic Radiosurgery, Medical Physics, vol. 35, No. 5, May 2008, pp. 2094-2103.
International Application No. CN201780072007.6, Office Action dated Jul. 3, 2020, 5 pages.

\* cited by examiner

CONTROLLING AND SHAPING THE DOSE DISTRIBUTION OUTSIDE TREATMENT TARGETS IN EXTERNAL-BEAM RADIATION TREATMENTS

CROSS-REFERENCE TO RELATED APPLICATIONS

The present application is a continuation of, and claims the benefit and priority to U.S. application Ser. No. 15/273,373, filed Sep. 22, 2016, now U.S. Pat. No. 10,143,859, issued Dec. 4, 2018, entitled "CONTROLLING AND SHAPING THE DOSE DISTRIBUTION OUTSIDE TREATMENT TARGETS IN EXTERNAL-BEAM RADIATION TREATMENTS," the contents of which is incorporated herein by reference for all purposes.

FIELD

The present disclosure relates generally to treatment planning for radiation therapy using external-beam radiation treatment systems, and is more particularly directed to controlling and shaping the dose distribution outside treatment targets.

BACKGROUND

In general, radiation therapy consists of the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used.

Modern radiation therapy techniques include the use of Intensity Modulated Radiotherapy ("IMRT"), typically by means of an external radiation treatment system, such as a linear accelerator, equipped with a multileaf collimator ("MLC"). Use of multileaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, the greater freedom which IMRT and other complex radiotherapy techniques, such as volumetric modulated arc therapy (VMAT, where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target, or possibly multiple targets, while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a radiation treatment plan.

The purpose of a normal tissue objective (NTO) in radiation treatment planning is to limit the amount of radiation to healthy tissues surrounding the treatment targets. In stereotactic radiosurgery (SRS) of the brain, the role of an NTO is even more important as the targets are contained within normal brain tissue, which is itself an organ at risk. Therefore, the clinical goals may include treating each target with its prescription and having the amount of absorbed dose decrease steeply to clinically insignificant levels as a function of distance perpendicular to the surface of the target so that normal tissue is minimally affected. The latter requirement is referred to as a "steep dose gradient."

Therefore, it is desirable to have efficient algorithms for controlling and shaping the dose distribution outside treatment targets in radiation treatment planning.

SUMMARY

According to embodiments of the present invention, streamlined and partially automated methods of setting normal tissue objectives in radiation treatment planning are provided. These methods may be applied to multiple-target cases as well as single-target cases. The need for contouring control structures around each target can be reduced or eliminated. Instead, the methods can impose one or more target-specific dose falloff constraints around each target, taking into account geometric characteristics of each target such as target volume and shape. In some embodiments, methods can also take into account a planner's preferences for target dose homogeneity. In some embodiments, methods can generate additional dose falloff constraints in locations between two targets where dose bridging is likely to occur.

Other embodiments are directed to systems and computer readable media associated with methods described herein.

A better understanding of the nature and advantages of embodiments of the present invention may be gained with reference to the following detailed description and the accompanying drawings.

TERMS

Figure 1:
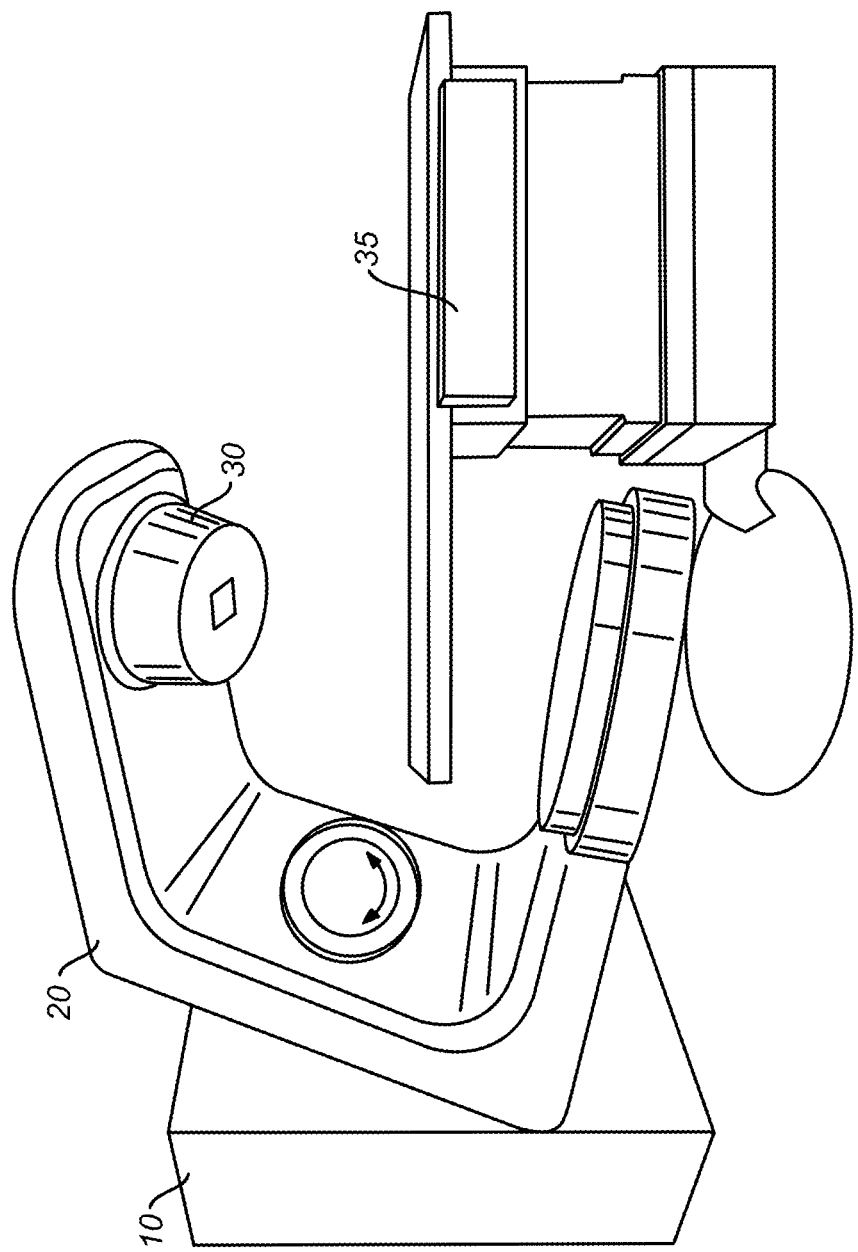
FIG. 1 is a schematic perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "radiation treatment plan" can include a dose distribution, machine parameters for achieving the dose distribution for a given patient, and information about the given patient. A dose distribution provides information about the variation in the dose of radiation with position. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

A "dose falloff region" can include voxels in a region immediately outside a target volume. A "dose falloff constraint profile" can include an upper dose constraint for each voxel outside a target volume. A "dose falloff constraint envelope" can include another upper dose constraint for each voxel outside the target volume. A "dose falloff constraint curve" can be a function of a distance away from and in a direction normal to the surface of a target volume that defines upper dose constraints outside a target volume.

DETAILED DESCRIPTION

The purpose of a normal tissue objective (NTO) in radiation treatment planning is to limit the amount of radiation to healthy tissues surrounding the treatment targets. In stereotactic radiosurgery (SRS) of the brain, the role of an NTO is even more important as the targets are contained within normal brain tissue, which is itself an organ at risk. Therefore, the clinical goals may include treating each target with its prescription and having the amount of absorbed dose decrease steeply to clinically insignificant levels as a function of distance perpendicular to the surface of the target. The latter requirement is referred to as a "steep dose gradient." The dose prescription typically depends on many factors, such as the volume of the target.

Some embodiments of the present invention provide streamlined and partially automated methods of setting normal tissue objectives in radiation treatment planning. These methods may be applied to multiple-target cases as well as single-target cases. The need for contouring control structures around each target can be reduced or eliminated. Instead, the methods can impose one or more target-specific dose falloff constraints around each target, taking into account geometric characteristics of each target such as target volume and shape. In some embodiments, methods can also take into account a planner's preferences for target dose homogeneity. In addition, the need for contouring control structures in dose bridging regions can also be eliminated. Instead, methods can generate additional dose falloff constraints in locations between two targets where dose bridging is likely to occur. According to some embodiments, the constraints can be designed in a way that may result in low isodose surfaces that are dilated, yet conformal, versions of those at higher dose levels. Furthermore, because embodiments can impose dose falloff constraints that are target-specific, having different dose prescriptions for different targets would not cause additional complications. Also, because the algorithms operate in dosimetric space, there would be no need to correct for suboptimally contoured control structures.

I. Treatment System

External beam therapy (EBT), also called external radiation therapy, is a method for delivering a beam or several beams of high-energy x-rays to a patient's tumor. Beams are generated outside the patient (usually by a linear accelerator) and are targeted at the tumor site.

Figure 2:
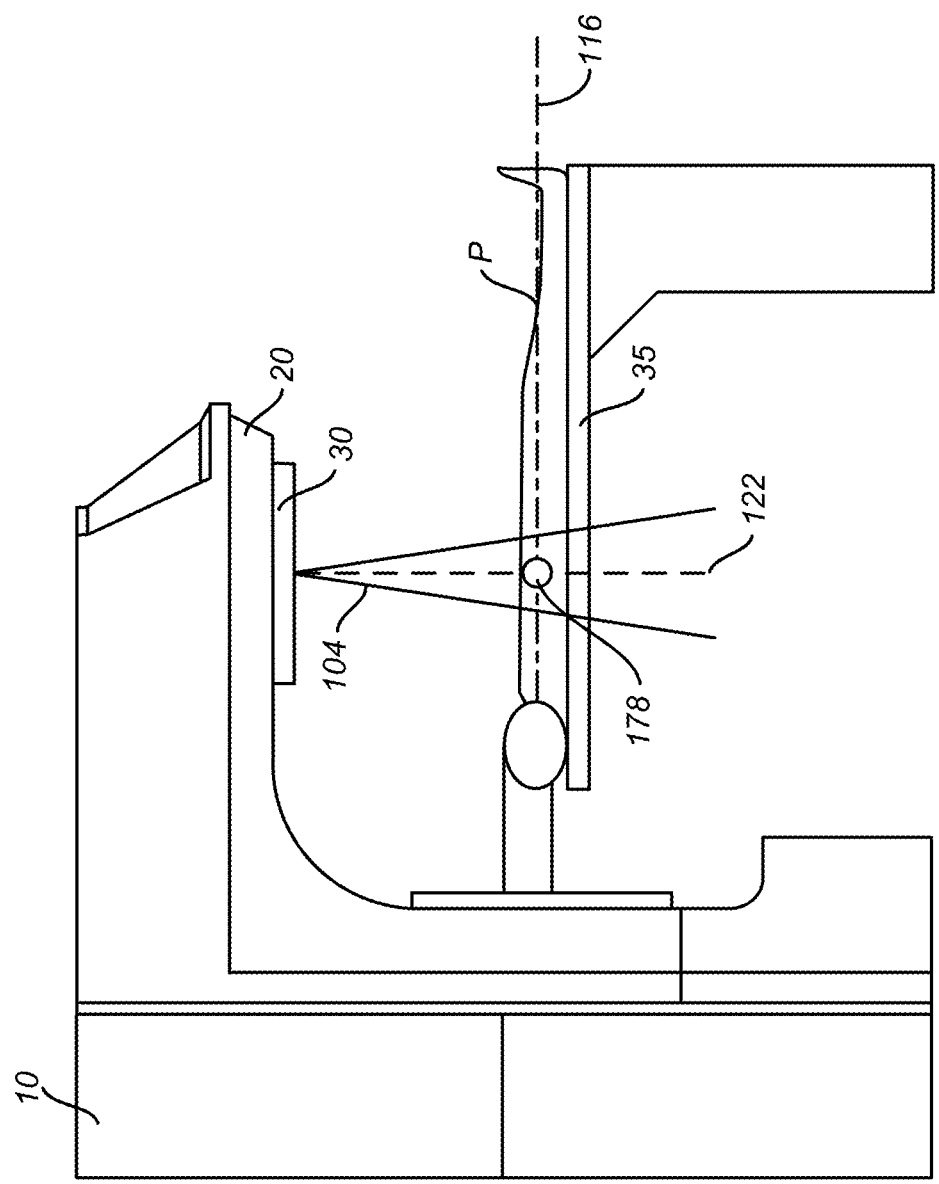
FIG. 2 is a schematic side view of a radiation treatment system.

FIGS. 1 and 2 depict a radiation treatment system of the type which may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type which may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
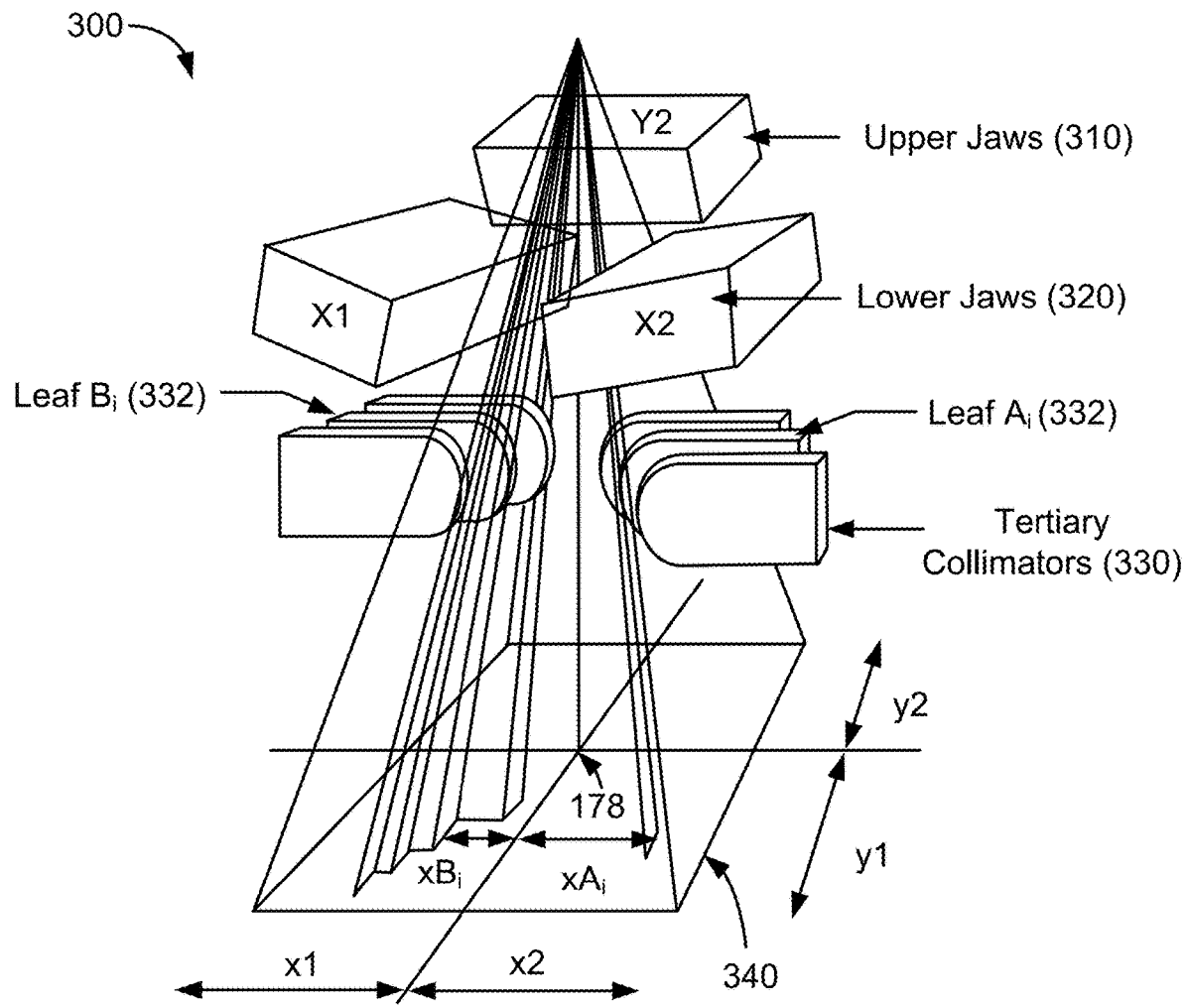
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
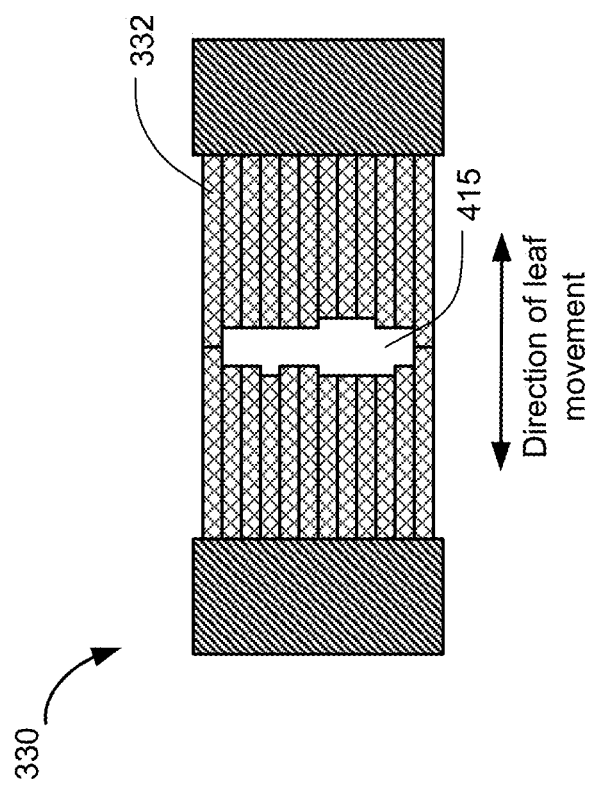
FIG. 4 shows an exemplary multileaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequence of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
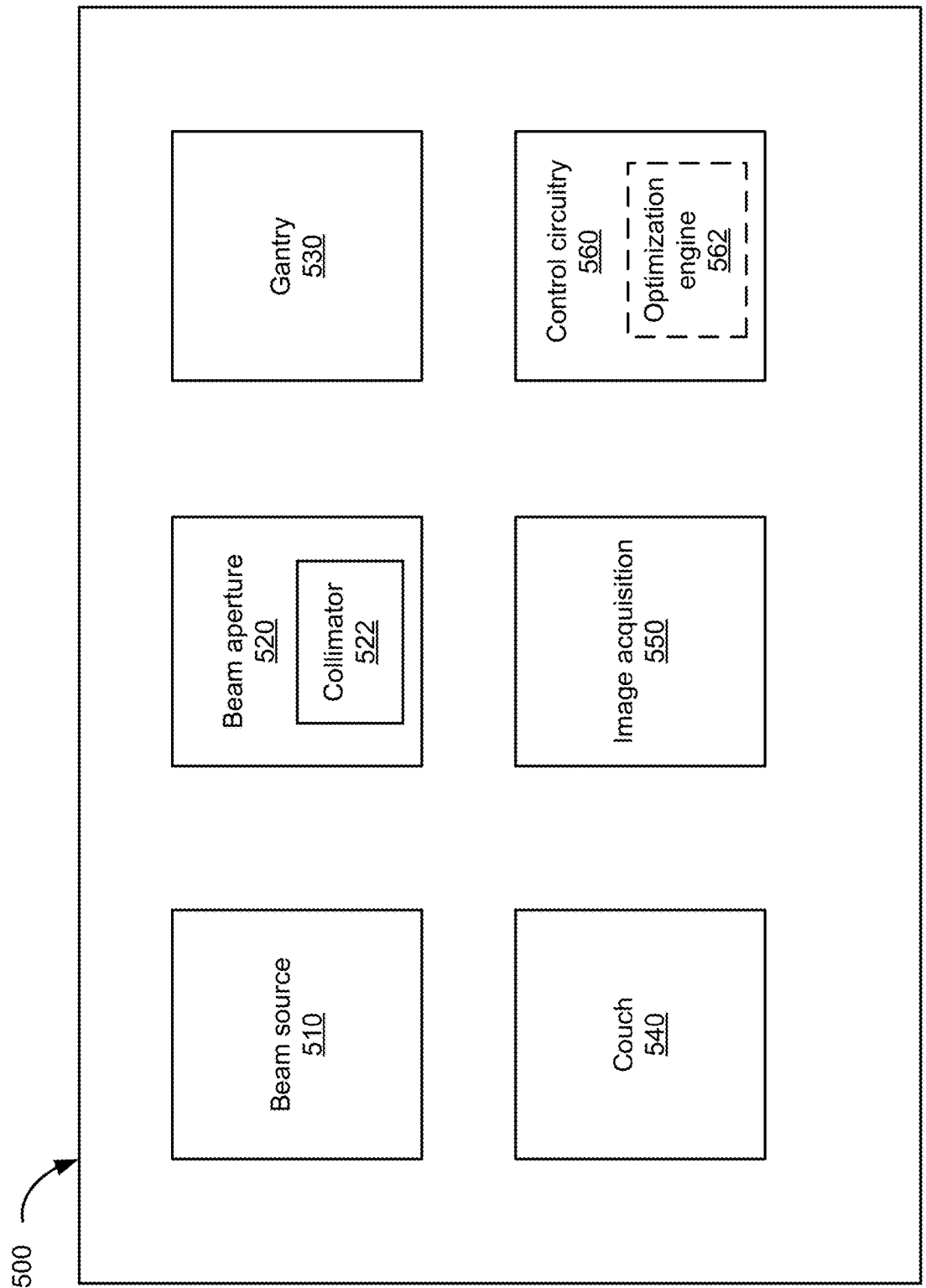
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Planning

Radiation therapy is generally implemented in accordance with a radiation treatment plan that typically takes into account the desired dose of radiation that is prescribed to be delivered to the tumor, as well as the maximum dose of radiation that can be delivered to surrounding tissue. Various techniques for developing radiation treatment plans may be used. Preferably, the computer system used to develop the radiation treatment plan provides an output that can be used to control the radiation treatment system, including the control points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans, such as volumetric modulated arc therapy (VMAT), where the one or more external treatment coordinates, such as the isocenter location, gantry angle, couch angles, and couch offsets, are in motion while irradiating the target volume. Heretofore, radiation oncologists or other medical professionals, such as medical physicists and dosimetrists, have used one of the available algorithms to develop and optimize a radiation treatment plan.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation without risk of damage. This volumetric information along with the prescribed dose limits and similar objectives set by the medical professionals are the basis for calculating an optimized dose distribution, also referred to as fluence map, which in turn is the basis for determining a radiation treatment plan. The volumetric information may, for example, be reduced to an objective function or a single figure of merit that accounts for the relative importance of various trade-offs inherent in a radiation treatment plan, along with constraints that must be met for the radiation treatment plan to be medically acceptable or physically possible.

Treatment planning algorithms can account for the capabilities of the specific radiation treatment system they are used with, for example, the energy spectrum and intensity profile of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

III. Controlling Dose Distribution Outside Treatment Targets

The purpose of a normal tissue objective (NTO) in radiation treatment planning is to limit the amount of radiation to healthy tissues surrounding the treatment targets. In stereotactic radiosurgery (SRS) of the brain, the role of an NTO is even more important as the targets are contained within normal brain tissue, which is itself an organ at risk. Clinical goals of a radiation treatment may include treating each target with its prescription and having the amount of absorbed radiation dose decrease steeply to clinically insignificant levels as a function of distance perpendicular to the surface of the target. The latter requirement is referred to as a "steep dose gradient."

A. Normal Tissue Objective

Figure 6:
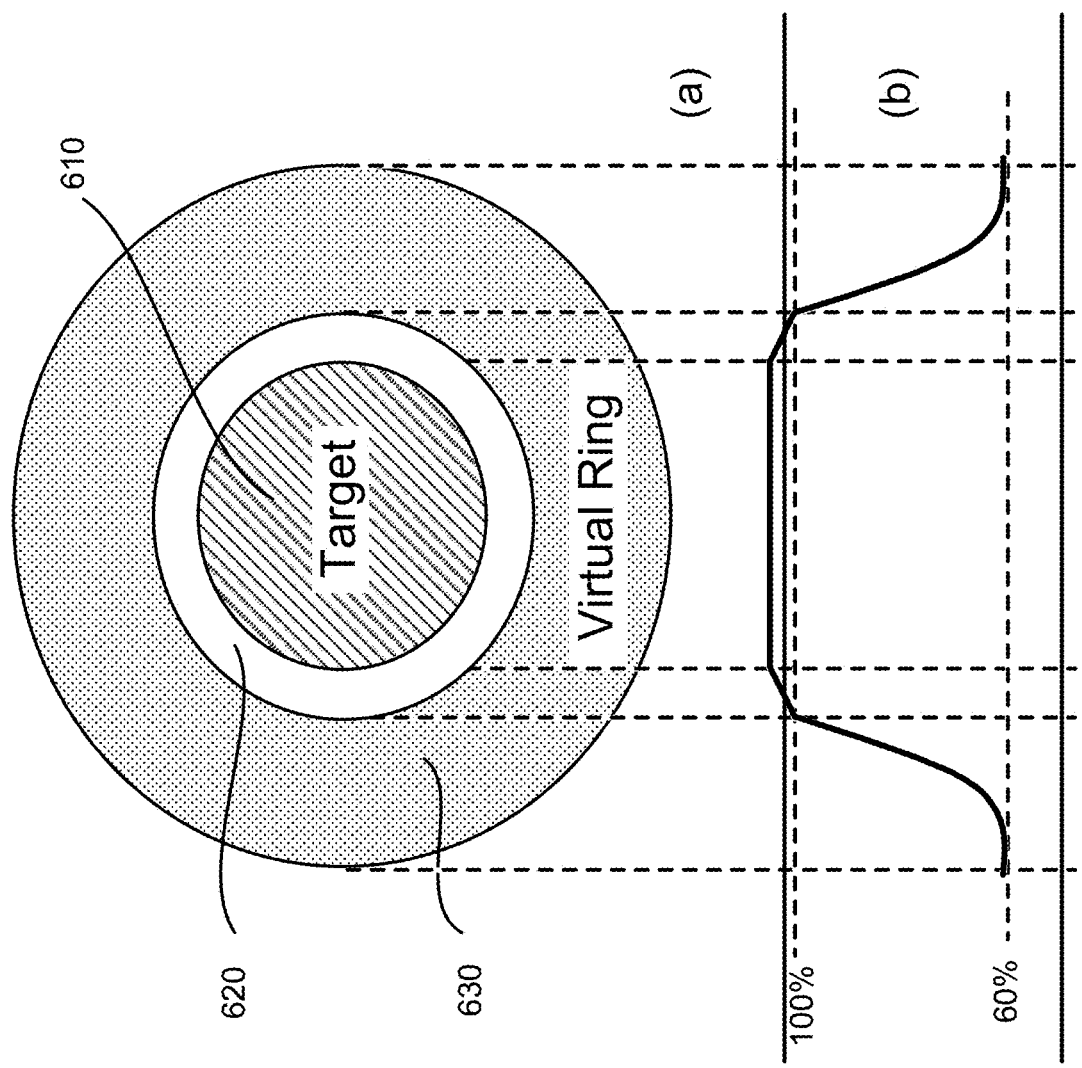
FIG. 6 illustrates (a) a schematic "virtual ring" of healthy tissue surrounding a target volume; and (b) a cross-section of an example dose distribution.

FIG. 6 illustrates (a) a schematic "virtual ring" 630 of healthy tissue surrounding a target volume 610; and (b) a cross-section of an example dose distribution. The dose distribution may be substantially homogeneous within the target volume 610 at a dose level slightly higher than the prescribed minimum dose value, and falls off to about 100% of the prescribed minimum dose value in the region 620 immediately outside the target volume, and falls off to about 60% of the prescribed minimum dose value at the outer boundary of the virtual ring 630 of healthy tissue. The thinner the virtual ring 630, the steeper the dose gradient outside the target volume 610.

When there are multiple targets within a domain of interest of a patient, radiation treatment planning may be more complicated than single-target cases. For example, for targets that are located close to each other, absorbed dose levels may be elevated in regions between the treatment targets in comparison to those at other locations at similar distances away from the treatment targets. This phenomenon is referred to as dose bridging. Dose bridging may occur as two or more targets are irradiated from a given direction of incidence. Thus, another objective of treatment planning might be requiring the prevention or reduction of dose bridging in multiple-target cases.

Figure 7:
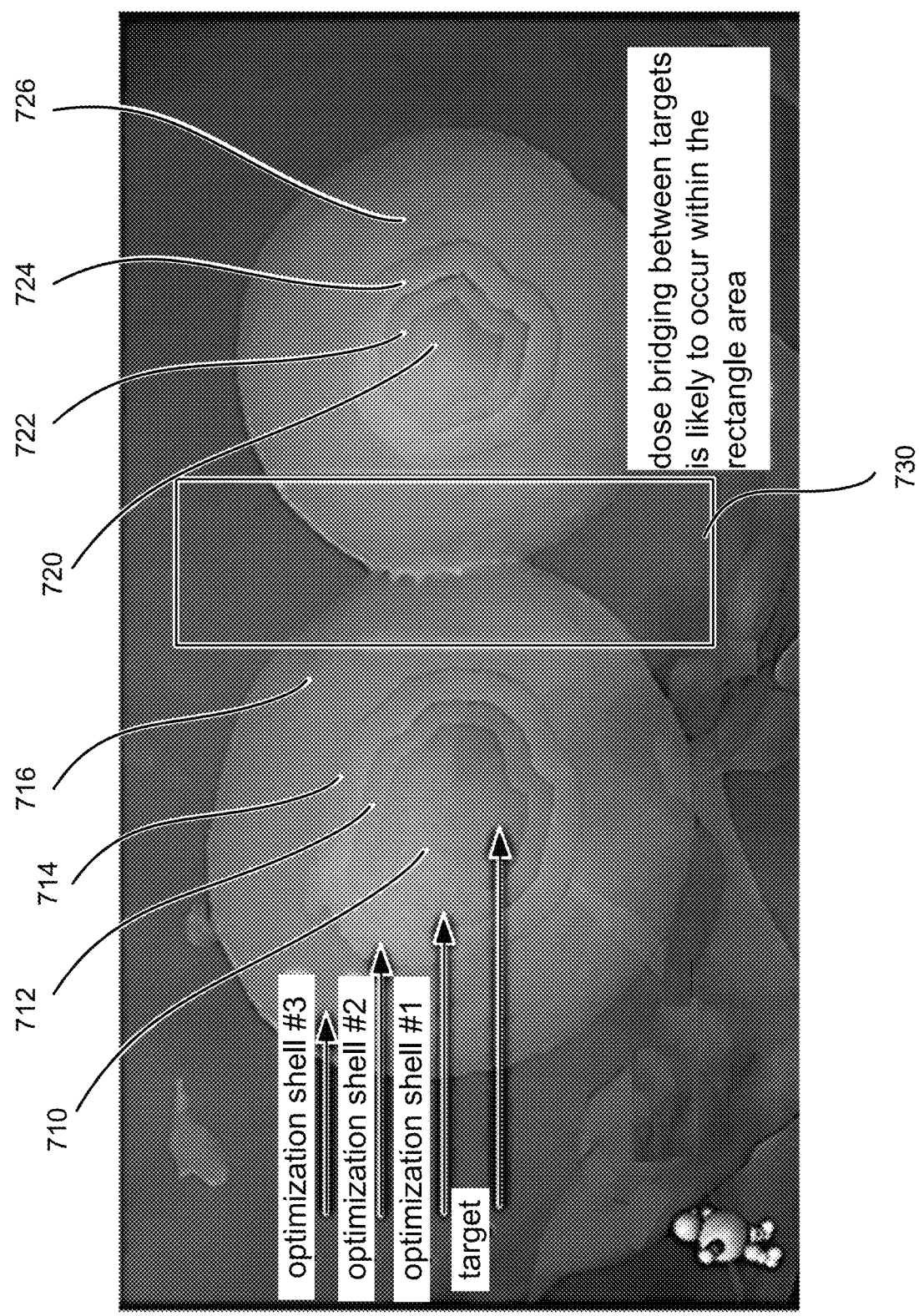
FIG. 7 shows an exemplary cross-sectional image of a cranial region of a patient.

FIG. 7 shows an exemplary cross-sectional image of a cranial region of a patient, where there are two metastasis targets 710 and 720. Conventionally, a radiation treatment planning typically starts with contouring the boundaries of the targets 710 and 720 and any organs-at-risk (OARs) in the vicinity of the targets. In radiation treatment of cranial targets, the normal tissue surrounding the targets may be considered an organ at risk. A planner may then set optimization objectives for each target based on physician's dose prescription. FIG. 7 is described in more detail below.

Figure 8:
FIG. 8 shows an exemplary graphic user interface where a planner may enter optimization objectives for the treatment targets.

FIG. 8 shows an exemplary graphic user interface for an optimization engine where a planner may enter optimization objectives for the targets. In this example, the planner has set a lower dose limit of 15.0 Gy for the target "PTV1" (i.e., 100% of the volume should receive at least 15.0 Gy), and a lower dose limit of 18.0 Gy for the target "PTV2" (i.e., 100% of the volume should receive at least 18.0 Gy). In this example, the planner has also set an upper dose limit of 16.17 Gy for the target "PTV1" (i.e., 0% of the volume should receive more than 16.17 Gy), and an upper dose limit of 19.4 Gy for the target "PTV2" (i.e., 0% of the volume should receive more than 19.4 Gy). In this example, the planner has set only a lower dose limit of 24.0 Gy for the target "PTV3" (i.e., 100% of the volume should receive at least 24.0 Gy).

In a conventional method, the planner may set normal tissue objectives by contouring control structures (also referred herein as optimization shells or optimization structures) around each target to ensure that radiation dose falls off fast enough outside the boundaries of the targets, so that normal brain tissues located outside the targets do not receive excessive radiation doses. For instance, in the example shown in FIG. 7, the planner may construct three optimization shells 712, 714, and 716 around the first target 710, and specify an upper dose limit for each of those optimization shells. For example, the planner may specify that any voxel inside the optimization shell 712 may not receive more than 90% of the lower dose limit prescribed for the first target 710, any voxel inside the optimization shell 714 may not receive more than 50% of the lower dose limit prescribed for the first target 710, and any voxel inside the optimization shell 716 may not receive more than 40% of the lower dose limit prescribed for the first target 710. Similarly, the planner may construct three optimization shells 722, 724, and 726 around the second target 720, and specify an upper dose limit for each of those shells.

In addition, for targets that are located close to each other, a planner may need to contour additional control structures for preventing dose bridging between targets. For instance, in the example illustrated in FIG. 7, dose bridging is likely to occur within the area 730 outlined by the red rectangle between the two targets 710 and 720. Thus, the planner may add local dose constraints in the dose bridging region 730.

Furthermore, the planner may need to optimize a treatment plan and iteratively recontour the control structures until a desired balance between target coverage, dose gradients, and healthy-tissue dose landscape has been attained. For example, the planner may need to adjust the thicknesses of one or more control structures and perform Boolean operations for each target for dose falloff control. The process may be further complicated by having different dose prescriptions for different targets. Thus, the planner may need to set optimization objectives and priorities for each control structure for all targets. This process may require expertise and involve manual work, and can be time consuming.

B. Virtual Cone Normal Tissue Objective (VCNTO)

Embodiments of the present invention provide streamlined and partially automated methods of setting normal tissue objectives in radiation treatment planning. These methods may be applied to multiple-target cases as well as single-target cases. In these methods, the need for contouring control structures around each target can be eliminated. Instead, the methods impose one or more target-specific dose falloff constraints around each target, taking into account geometric characteristics of each target such as target volume and shape. In some embodiments, the methods also take into account a planner's preferences for target dose homogeneity. In addition, the need for contouring control structures in dose bridging regions can also be eliminated. Instead, the methods generate additional dose falloff constraints in locations where dose bridging is likely to occur. According to some embodiments, the constraints are designed in a way that may result in low isodose surfaces that are dilated, yet conformal (i.e. they retain approximately the shape of the high-isodose surfaces), versions of those at higher dose levels. Furthermore, because the methods impose dose falloff constraints that are target-specific, having different dose prescriptions for different targets would not cause additional complications. Also, because the algorithms operate in dosimetric space, there would be no need to correct for suboptimally contoured control structures.

Figure 9:
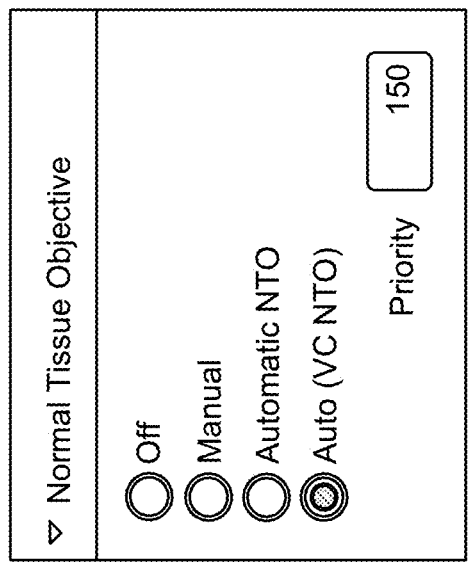
FIG. 9 illustrates an exemplary graphic user interface for using a Virtual Cone Normal Tissue Objective (VCNTO) algorithm in planning a radiation treatment according to one embodiment of the present invention.

FIG. 9 illustrates an exemplary graphic user interface for an optimization engine using a Virtual Cone Normal Tissue Objective (VCNTO) algorithm in planning a radiation treatment according to one embodiment of the present invention. A user may select "Auto (VC NTO)" and set an optimization priority. The algorithm would automatically generate target-specific dose falloff constraints. There is no need to contour controlling structures as in conventional methods.

1. Target-Specific Dose Falloff Constraints

Figure 10:
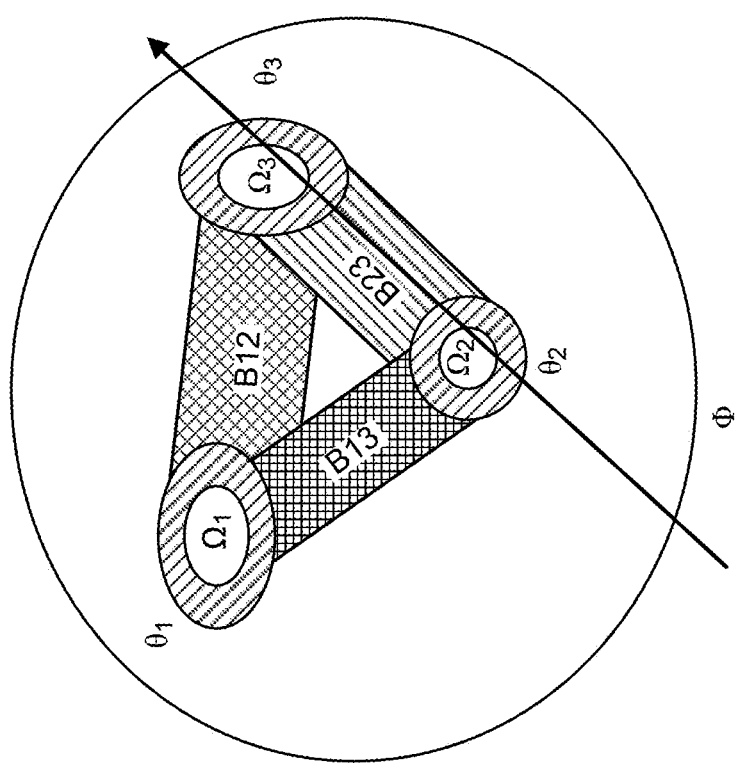
FIG. 10 illustrates an exemplary treatment geometry wherein there are three treatment targets in a domain of interest within a patient.

FIG. 10 illustrates an exemplary treatment geometry. $\Phi$ is the domain of interest, i.e., the imaged part of the patient. In this example, there are three targets $\Omega_1$, $\Omega_2$, and $\Omega_3$ in the domain of interest $\Phi$. In a general case, assume that there are N targets in a domain of interest $\Phi$. According to some embodiments, VCNTO features an explicit dose falloff region $\Theta_t$ about each target t. In one embodiment, $\Theta_t$ may be defined by, $$\Theta_t(T) = \{r | 0 < d_t(r) \leq \theta_t(T)\},$$

where $d_t(r)$ is a function that provides the shortest distance to the surface of target t from coordinate r, and $\theta_t(T)$ defines the geometric extent of the dose falloff region. The target regions $\{\Omega_t\}$ and the dose falloff regions $\{\Theta_t(T)\}$ are contained within a domain of interest $\Phi$. $\Theta_t(T)$ is introduced in order to facilitate individual control over the local dose landscape about each target at close proximity.

VCNTO is designed such that it produces treatment plans that feature steep dose decay in space from target-specific prescriptions to a low asymptotic, clinically insignificant dose level common to all targets at spatial coordinates far from any target. This applies to the case of multiple treatment targets and the regions of space between treatment targets, as well as to single-target cases. VCNTO can be initialized in the preprocessing stage of the optimization. It takes the detailed volumetric structure of each treatment target and associated target-specific optimization objectives as input. The imposed requirement on dose falloff is a function of the shape and size of targets, as well as their relative positions. VCNTO assumes that any target that is provided as input does not include spatially disjoint parts. If the treatment target includes N spatially disjoint regions, they must be converted to N separate targets by the planner for VCNTO to function as intended.

VCNTO may also be reinitialized during optimization at any iteration. This aspect is taken into consideration in the equations above by the dependence on the time parameter T. In some embodiments, re-initialization may be prompted by a local under-dosing of a target. In such cases, the VCNTO algorithm may adjust the dose falloff constraints in the vicinity of the under-dosed part of the target. In some other embodiments, re-initialization may be prompted where the dose falloff constraints imposed by VCNTO are met locally. In such cases, the VCNTO algorithm may make local corrections to the constraint and weights to steepen the spatial dose gradient locally even more.

In some embodiments, the VCNTO may include a set of upper dose constraints indexed with i=1, 2, . . . that are weighted in importance. A spatial upper dose constraint $c_{i,t}(r,T)$ constrains dose values at each coordinate r at time T within the domain of interest $\Phi$, with respect to target t. The upper dose constraint $c_{i,t}(r,T)$ represents a term in a cost function that is used in optimizing a treatment plan. In one embodiment, $c_{i,t}(r,T)$ may be expressed as, $$c_{i,t}(r,T) = \max\{0, (D(r,T) - D_{i,t}(r,T))/D_0\}^2 \tag{1}$$

where $D(r,T)$ is the actual dose level at location r at time T, $D_{i,t}(r,T)$ is the dose falloff constraint profile imposed by the $i^{th}$ constraint with respect to target t, and $D_0$ is a constant reference dose level for making the constraint a dimensionless quantity. According to Equation (1), $c_{i,t}(r,T)$ would have a value of zero if $D(r,T) \leq D_{i,t}(r,T)$, and has a positive value if $D(r,T) > D_{i,t}(r,T)$. The value of the term $c_{i,t}(r,T)$ represents a cost penalty that increases as square of the actual dose level $D(r,T)$ in excess of the value of the dose falloff constraint profile $D_{i,t}(r,T)$ at the same coordinate r. In other embodiments, $c_{i,t}(r,T)$ may have a positive value that increases as other functions of the actual dose level $D(r,T)$ in excess of the value of the dose falloff constraint profile $D_{i,t}(r,T)$ at the same coordinate r. For example, it may be a polynomial function of an order greater than two, or an exponential function.

In some embodiments, the constraint $c_{i,t}(r,T)$ may have an associated cost function $C_{i,t}(r,T)$ expressed as, $$C_{i,t}(r,T) = w_{i,t}(r,T) c_{i,t}(r,T) \tag{2}$$

where $w_{i,t}(r, T)$ is a weight factor that controls the cost relative to the local neighborhood of point r. The total cost in the domain of interest $\Phi$ due to the $i^{th}$ constraint can be expressed as, $$C_{i,t}(T) = P_{i,t} \Sigma_{r \in \Phi} C_{i,t}(r,T) \tag{3}$$

where $P_{i,t}$ is the priority for the $i^{th}$ constraint for target t.

2. Adaptation of Dose Constraints According to Planner's Planning Style

In some embodiments, an algorithm may adapt to different planning styles. Different planners may have different preferences in terms of dose homogeneity (or heterogeneity) within a target. For example, a neurosurgeon may not be particularly concerned about dose levels inside a target being higher than a prescribed minimum dose, as he may be concerned mainly about destroying the tissues within the target with radiation. Thus, he may set only a lower dose limit within the target without setting an upper dose limit within the target. On the other hand, a radiation treatment clinician may be more cautious about dose homogeneity inside a target, and may set an upper dose limit as well as a lower dose limit within a target.

For instance, in the example shown in FIG. 8, the planner only set a lower dose limit but did not set an upper dose limit for the target "PTV3." In comparison, the planner set both a lower dose limit and an upper dose limit for the targets "PTV1" and "PTV2." In this example, the lower dose limit for "PTV1" is set to 15.0 Gy (i.e., 100% of the volume should receive at least 15.0 Gy), and the upper dose limit for "PTV1" is set to 16.17 Gy (i.e., 0% of the volume should receive more than 16.17 Gy). In this example, the lower dose limit for "PTV2" is set to 18.0 Gy (i.e., 100% of the volume should receive at least 18.0 Gy), and the upper dose limit for "PTV2" is set to 19.4 Gy (i.e., 0% of the volume should receive more than 19.4 Gy). Therefore, for the target "PTV1" and "PTV2," the level of dose heterogeneity is limited to about 7.8% (i.e., (19.4−18.0)/18.0≈0.078, (16.17−15.0)/15.0=0.078). But no dose heterogeneity is specified for the target "PTV3."

Figure 11:
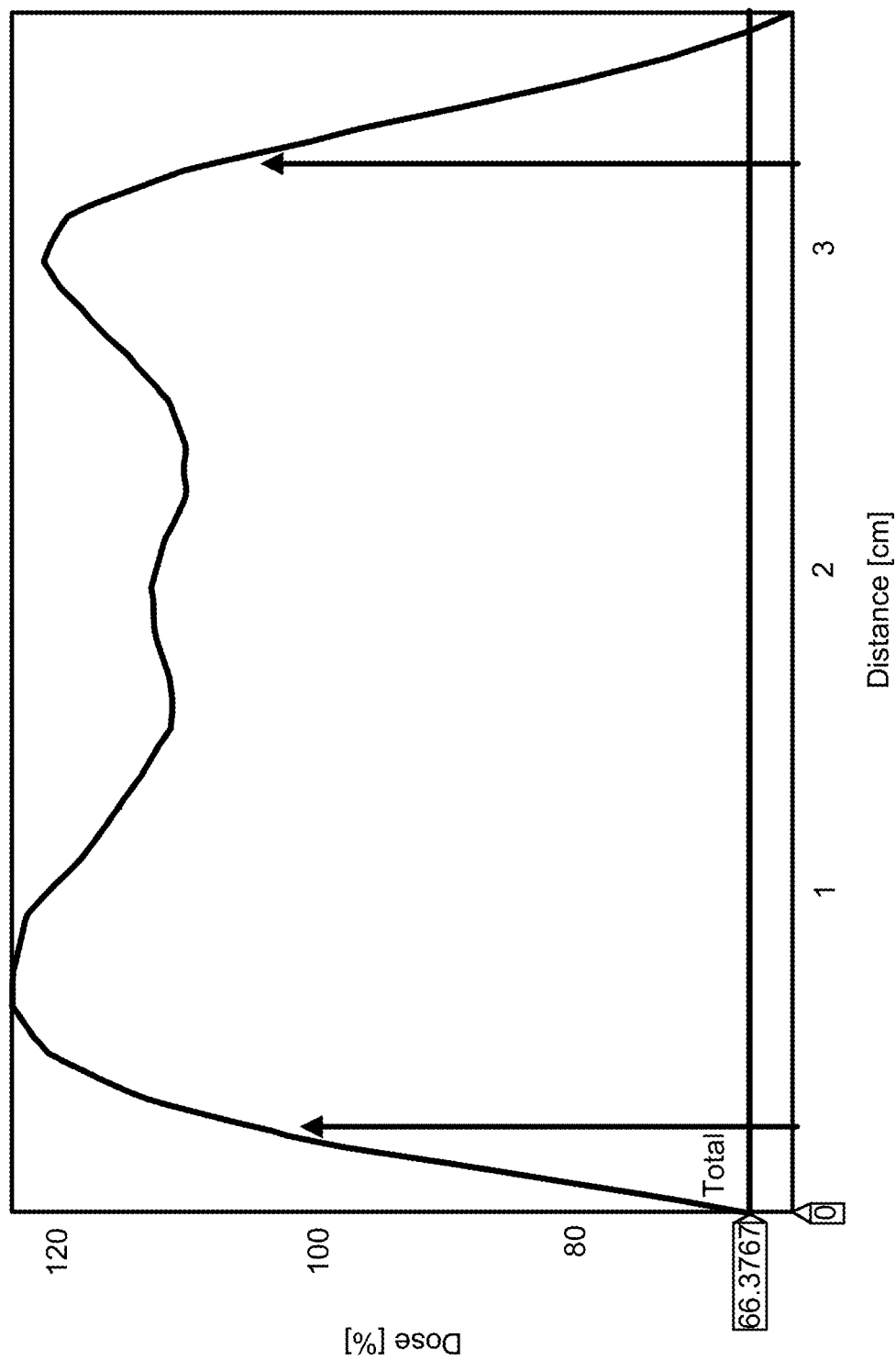
FIG. 11 shows an exemplary dose distribution inside a target volume.

Planning style has an indirect effect on how steeply the dose level can decay perpendicular to the target surface just outside the target. FIG. 11 shows an exemplary dose distribution within a target volume. The arrows indicate the positions of the surface of the target volume. As shown in FIG. 11, dose levels inside a target may tend to peak near the surface of a target. If no upper limit is set for the dose level inside a target, a steeper falloff just outside the target might be possible. On the other hand, if an upper limit is set for the dose level inside a target, the dose falloff outside the target may need to be more gradual so that the dose heterogeneity inside the target does not exceed the prescribed value.

The VCNTO algorithms may take a planner's style into account. In some embodiments, an algorithm may interpret a planner's preferences based on whether he has set lower and upper dose limits for a target, and what their priorities are. For example, if a planner has not set an upper dose limit for a target, the algorithm may assume that the planner strives for a maximally steep dose falloff. The algorithm then generates the dose falloff constraint profile outside the target accordingly. On the other hand, if a planner has set both a lower dose limit and an upper dose limit for a target, the algorithm may impose a limit to the dose gradient steepness just outside the target so as to keep the dose heterogeneity inside the target below the prescribed level. For example, if the planner has not set an upper dose limit for a target, the VCNTO algorithm may generate a dose falloff constraint profile that would cause the dose value to fall to 1/e (or about 40%) of the prescribed lower limit at a distance of about 3 mm away from the surface of the target. Whereas, if the planner has set both an upper dose limit and a lower dose limit for a target, the VCNTO algorithm may generate a dose falloff constraint profile that would cause the dose value to fall to 1/e (or about 40%) of the prescribed lower dose limit at a distance about 8 mm, as compared to 3 mm, away from the surface of the target, so that the prescribed dose homogeneity is attained.

In general, the VCNTO algorithm may analyze the user-specified optimization objectives for each target. Optimization objectives for targets t=1, 2, . . . N may describe what the minimum dose level, $D_{min}(t)$, and maximum dose level, $D_{max}(t)$, in the target t should be, and what the relative priorities of meeting those objectives are. The ratio $H_t=D_{max}(t)/D_{min}(t)$ describes the planner's tolerance of dose heterogeneity inside the target t. The ratio $H_t$ and the volume of the target effectively determine the maximal attainable steepness of the dose distribution as a function of the distance normal to the surface of the target. The priorities $P_i$ of Equation (3) are set based on input from the user.

If the planner changes the optimization objectives during optimization such that the previous calibration of VCNTO parameters is no longer compatible with the planner's goals (as determined based on the new set of objectives), a recalibration of VCNTO may be carried out. This aspect is taken into consideration in the equations above by the dependence on the time parameter T. In some embodiments, recalibration may be performed where the planner has begun the optimization without limitations on the degree of dose heterogeneity inside the targets, and the planner then decides to add such a limitation during the optimization process.

3. Geometric Considerations and Specification of Dose Constraints

According to some embodiments, for each target t, a set of dose falloff constraint profiles $D_{i,t}(r,T)$, i=1, 2, . . . may be generated. The value $H_t$, the volume of target t, and the number of targets are used as guidance for setting $D_{i,t}(r,T)$. The subscript t is introduced to indicate target-specificity.

The mathematical expressions for the dose decay profiles $D_{i,t}(r, T)$ may depend on the planning style, and the volume and the shape of the target. In some embodiments, the starting point for the imposed dose falloff constraint profiles $D_{i,t}(r, T)$ may be an exponential function expressed as, $$D_{1,t}(r, T) = \begin{cases} \alpha_t A_{0t}(T), & 0 \le d_t(r) \le s_{1,t}(T) \\ (A_{0t}(T) - A_{1,\infty})\exp\left(-\frac{d_t(r) - s_{1,t}(T)}{\delta_t}\right) + A_{1,\infty}, & d_t(r) > s_{1,t}(T) \end{cases}, \quad (4)$$

where $\alpha_t$ is referred to as the gap coefficient, $s_{1,t}(T)$ is the linear size of the region about target t inside which a constant dose level of $\alpha_t A_{0t}(T)$ is imposed, $\delta_t$ is the decay length, and $A_{1,\infty}$ is the asymptotic dose level that does not depend on t.

In one embodiment, one may choose $\alpha_t=1$, $s_{1,t}=0$, $\delta_t=\min\{10 \text{ mm}, \max\{3 \text{ mm}, (1/2)(V(\Omega_t)/(4\pi/3))^{1/3}\}\}$, $A_{1,\infty}=(1/4) \max_t D_P(t)$, and $A_{0t}=D_P(t)$, where $D_P(t)$ is the lower dose limit of dose prescription for target t. In other embodiments, these parameters may be set to other values. For example, $A_{1,\infty}$ may be set to be 15% of the greatest dose prescription among the targets [i.e., $A_{1,\infty}=(0.15) \max_t D_P(t)$] in another embodiment. The decay length $\delta_t$ may be set to different values depending on factors such as planning style, as discussed above.

Figure 12:
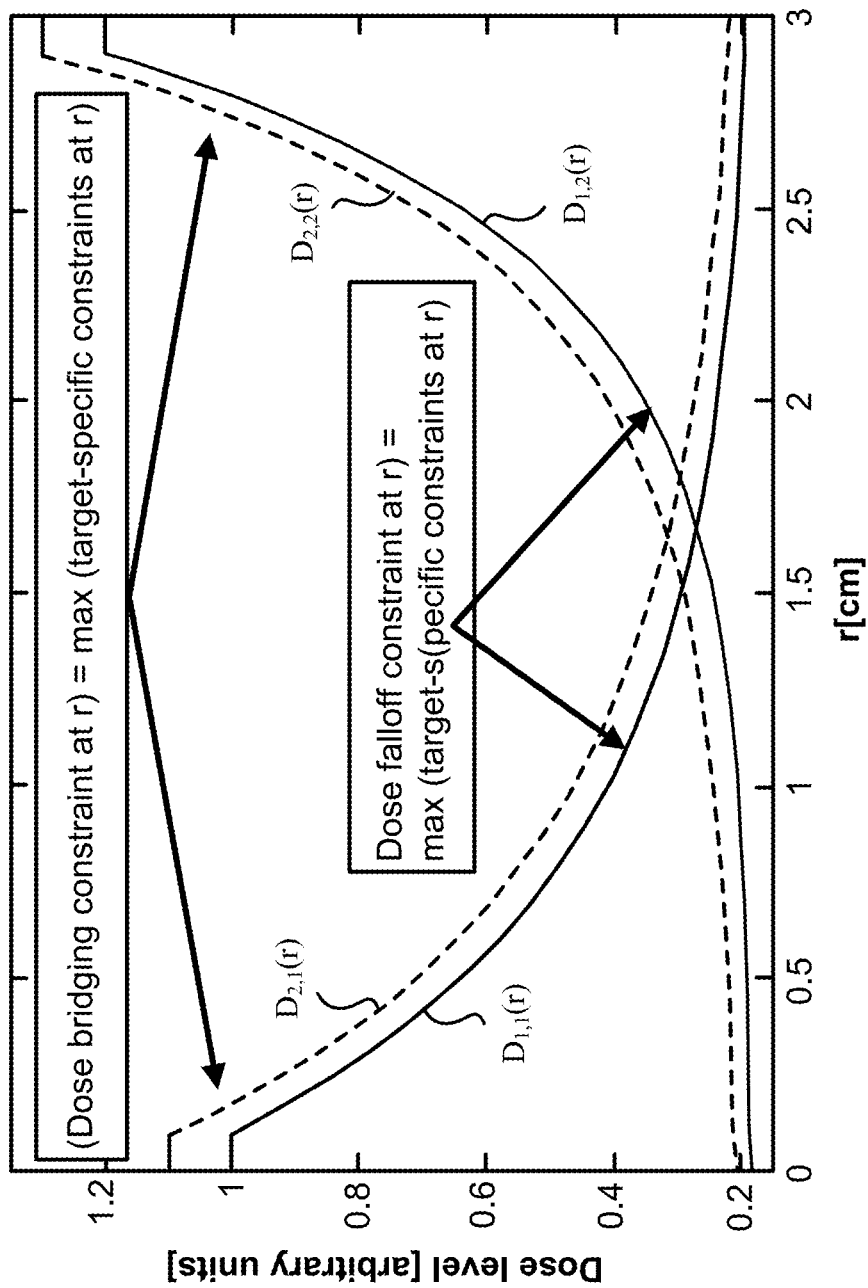
FIG. 12 illustrates exemplary dose falloff constraint curves that a VCNTO algorithm may generate according to embodiments of the present invention.

FIG. 12 illustrates exemplary dose falloff constraint curves that a VCNTO algorithm may generate according to an embodiment. In this example, there are two targets whose surface boundaries are located at r=0 cm and r=3.0 cm, respectively. The dose prescriptions for the two targets $D_P(1)$ and $D_P(2)$ are 1.0 and 1.2, respectively, in arbitrary units. The solid curves $D_{1,1}(r)$ and $D_{1,2}(r)$ are the dose falloff constraint profiles for the first target and the second target, respectively.

In some embodiments, each of the dose falloff constraint profiles $D_{1,1}(r)$ and $D_{1,2}(r)$ may decay asymptotically to a predetermined value $A_{1,\infty}$ at distances far from any target. The predetermined value $A_{1,\infty}$ may be defined as a percentage of the greatest dose prescription among all the targets $\max_t D_P(t)$. For instance, in the example illustrated in FIG. 12, $A_{1,\infty}$ may be set to be 15% of 1.2 (i.e., 0.15*1.2=0.18, in arbitrary unit).

In one embodiment, one may employ the following model for the weight $w_{1,t}(r,T)$ associated with $D_{1,t}(r,T)$, $$w_{1,t}(r,T)=\beta_t(d_t(r),H_t)w(T,\{\Theta_t\},H_t) \quad (5)$$

where $\beta_t$ is a target-specific smoothing function with values in the range [0,1], and w is a weighting scheme, which is a function of the set of treatment targets $\chi$, their dose falloff regions and heterogeneity requirements. In one embodiment, $\beta_t=1$, and $w(r,T)=1/V(\Omega_t)$ for $r \in \Theta_t(T)$, where $V(\Omega_t)$ is the volume of target t, and $w(r,T)=1/V(\Phi \setminus \chi)$ for $r \in \Phi \setminus \Theta_t(T)$. In other embodiments, other choices of weighting may be made.

In one embodiment, the dose falloff constraint profile $D_t(r,T)$ and the weights $w_t(r,T)$ stay constant in time throughout the optimization process. In an alternative embodiment, if not all points inside a $t^{th}$ target receive the prescribed dose within a threshold value, an attempt to reduce the under-dosing can be made by decreasing the local weight value $w_{1,t}(r,T)$ and/or by increasing dose levels $D_{1,t}(r,T)$ in the vicinity of the under-dosed part of the target in $\Omega_t$. Such an adjustment can be carried out periodically during the optimization. The priorities $P_{i,t}$ are initialized as well, and they may remain user-adjustable during the optimization.

In the case of a single treatment target, the index t is unnecessary. Thus $w_{i,t}(r, T)$ and $D_{i,t}(r,T)$ may be expressed as $w_i(r, T)$ and $D_i(r,T)$.

4. Multiple Treatment Targets

The case of multiple treatment targets within the domain of interest is more complicated than the single-target case. In some embodiments, the target-specific dose falloff constraint profiles $\{D_{i,t}(r,T)\}$ may be mapped to a single value at each coordinate r as, $$D_i(r,T)=f_i(\{D_{i,t}(r,T)\}) \quad (6)$$

$$w_i(r,T)=g_i(\{w_{i,t}(r,T)\}) \quad (7)$$

where $f_i$ and $g_i$ are mapping functions for the $i^{th}$ constraint.

In one embodiment, $D_i(r,T)$ may be set to be the maximum value among $\{D_{i,t}(r,T)\}$ for all targets, and $w_i(r, T)$ may be set to be the maximum value among $\{w_{i,t}(r, T)\}$ for all targets, for a given coordinate r. That is, $$D_i(r,T)=\max_t(\{D_{i,t}(r,T)\}) \quad (8)$$

$$w_i(r,T)=\max_t(\{w_{i,t}(r,T)\}) \quad (9)$$

For instance, in the example illustrated in FIG. 12, the two dose falloff constraint profiles $D_{1,1}(r)$ and $D_{1,2}(r)$ overlap in the region between the two targets. In one embodiment, the value of the dose falloff constraint profile $D_1(r)$ at a given coordinate r is the greater of the values of the two dose falloff constraint profiles $D_{1,1}(r)$ and $D_{1,2}(r)$ at the respective coordinate r. For example, at r=1.0, the value of $D_1(r=1.0)$ would be the value of the dose falloff constraint profile $D_{1,1}(r=1.0)$. On the other hand, at r=2.0, the value of $D_1(r=2.0)$ would be the value of the dose falloff constraint profile $D_{1,2}(r=2.0)$.

a) Dose Bridging Controller

Dose bridges are regions between treatment targets in which the absorbed dose levels are elevated in comparison to those at other locations at similar distances away from the treatment targets. Dose bridging may occur when treatment beam irradiates at least two targets from a given direction of incidence. For instance, in the example shown in FIG. 10, the regions between pairs of targets $B_{12}$, $B_{13}$, and $B_{23}$ are potential dose bridging regions. The arrow is an example direction of incidence that may result in dose bridging in region $B_{23}$ between targets $\Omega_2$ and $\Omega_3$. For directions of incidence in which at least two targets line up, a cost-function-based optimizer may try to find the minimum cost by balancing between irradiation of both targets and irradiation of normal tissues in front, between, and behind the targets. Increasing irradiation of the targets reduces the cost, whereas increasing irradiation of normal tissues increases the cost.

In conventional optimization methods, a planner usually adjusts dose bridges manually by contouring optimization structures and defining DVH-based upper constraints for each of them. In contrast, VCNTO algorithms achieve reduction or elimination of dose bridging above clinically relevant levels by imposing a second upper dose constraint $c_2(r,T)$. In some embodiments, the second upper dose constraint $c_2(r,T)$ may have a dose falloff constraint profile $D_{2,t}(r,T)$ that sits above $D_{1,t}(r,T)$. $D_{2,t}(r,T)$ is referred to as a dose falloff constraint envelope, and may be expressed as, $$D_{2,t}(r,T)=D_{1,t}(r,T)+\Delta_t(d_t(r)) \quad (10)$$

where $\Delta_t(d_t(r))$ is a non-negative quantity. In some embodiments, $\Delta_t(d_t(r))$ may be set as a predetermined percentage of the dose prescription for target t. For example, $\Delta_t(d_t(r))$ may be set as $\Delta_t(d_t(r))=D_P(t)/10$. In other embodiments, other percentage values may be chosen.

In one embodiment, the dose bridging region between targets t=1 and t=2 can be defined to be the convex hull of t=1 and t=2 with the target regions $\Omega_1$ and $\Omega_2$ removed from it. Inside the collection of dose bridging regions, denoted as B, the mapping functions $f_2$ and $g_2$ of Equations (6) and (7) can be chosen, for instance, to be, $$D_2(r,T)=\max_t(\{D_{2,t}(r,T)\}) \quad (11)$$

$$w_2(r,T)=1/V(B) \quad (12)$$

for $\{r | r \in B, B \subset B\}$, where V(B) denotes the volume of the collection of dose bridge regions.

For instance, in the examples shown in FIG. 12, the two dashed curves $D_{2,1}(r)$ and $D_{2,2}(r)$ are the dose falloff constraint envelopes for the two targets t=1 and t=2 located at r=0 and 3.0, respectively. For regions where the two dose falloff constraint envelopes $D_{2,1}(r)$ and $D_{2,2}(r)$ overlap, the value of $D_2(r)$ may be set as the greater of the values of the two dose falloff constraint envelopes $D_{2,1}(r)$ and $D_{2,2}(r)$ at the respective distance r. For example, at r=1.0, the value of $D_2(r=1.0)$ would be the value of $D_{2,1}(r=1.0)$. On the other hand, at r=2.0, the value of $D_2(r=2.0)$ would be the value of $D_{2,2}(r=2.0)$. Outside of the dose bridging regions, one may choose $D_2(r,T)$ and $w_2(r, T)$ as in the single-target case.

In some embodiments, the VCNTO algorithm may automatically limit the level of dose bridging between targets asymptotically to a predetermined percentage of the highest target-specific prescription. For instance, for the example illustrated in FIG. 12, a VCNTO algorithm may limit the level of dose bridging between the two targets to 15% of 1.2 (i.e., 0.15*1.2=0.18). In some embodiments, as the surface-to-surface distance between two targets decreases, the tolerated level of dose bridging may increase so as not to prevent the targets from attaining their respective dose prescriptions. In effect, a dose falloff constraint envelope or the "dose bridging controller" guides the optimizer not to irradiate more than one target with a given beamlet.

In some embodiments, the weighting function for the envelope, $w_{2,t}(r, T)$ has a general form identical to that of $w_{1,t}(r, T)$ in Equation (5) as above. In one embodiment, $w_{2,t}(r, T)$ may be set as, $w_{2,t}(r, T)=0$ for $r \in \cup_{t \in T} \Omega_t$, and $w_{2,t}(r, T)=1/V (\Phi \backslash \notin_{t \in T} \Omega_t)$ for $r \in \Phi \backslash \cup_{t \in T} \Omega_t$.

In some embodiments, $w_{2,t}(r, T)$ may be set to be significantly greater than $w_{1,t}(r, T)$, so that a greater penalty is imposed for any dose value in excess of the envelope $D_2(r)$ as compared to the penalty for any dose value in excess of the dose falloff constraint $D_1(r)$. Thus, the dose falloff constraint envelope $D_2(r)$ may provide a hard ceiling for the maximal accepted dose level in the dose bridging regions. In one embodiment, $w_{2,t}(r, T)$ may be set to be about twice of $w_{1,t}(r, T)$.

b) Dose Bridging Controller Between Targets at Very Close Proximity

In some embodiments, for two targets that are very close to each other, for example, with a surface-to-surface distance less than about 5 mm, the VCNTO algorithm may place a local dose constraint about halfway between the two targets. In one embodiment, the VCNTO algorithm may penalize any dose values in excess of a predetermined fraction, for example 0.5-0.75, of the greater of the dose prescriptions for the two targets.

Figure 13:
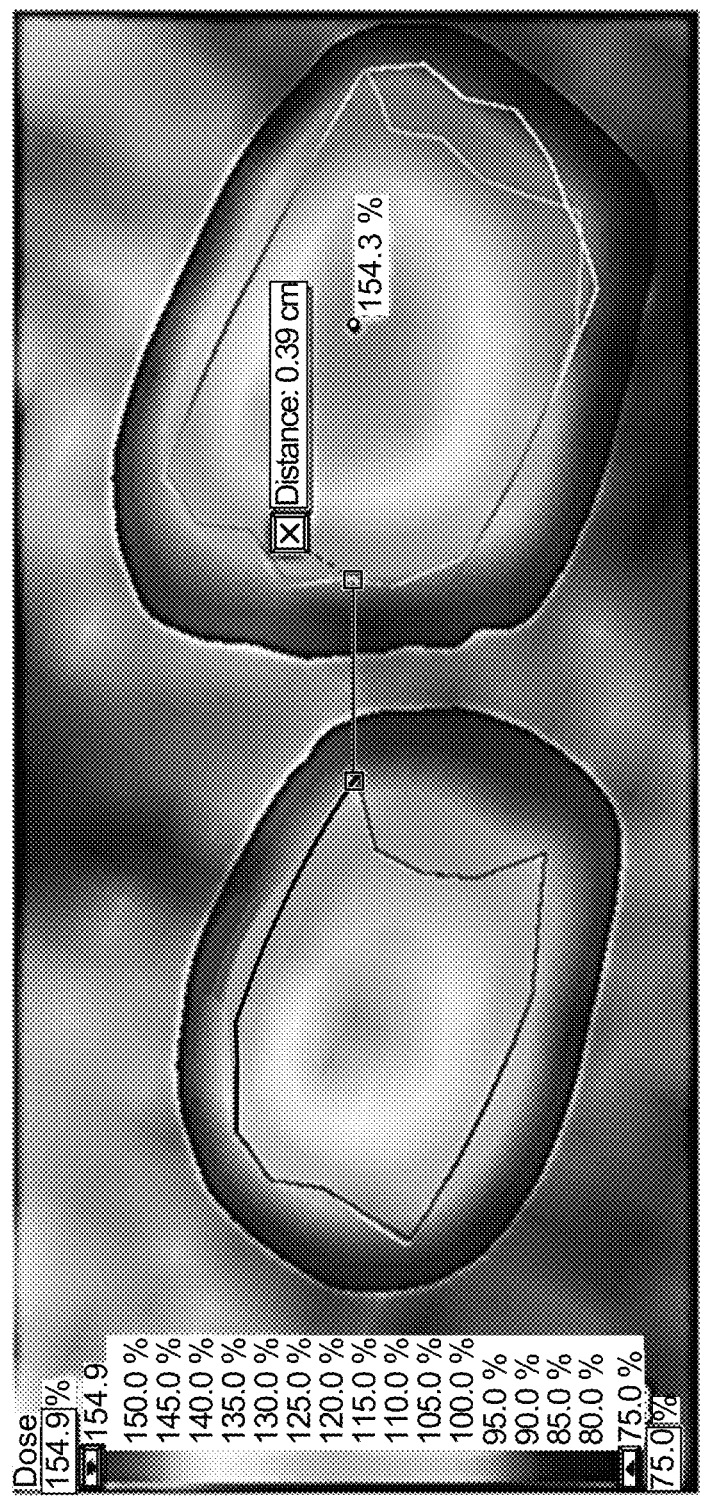
FIG. 13 illustrates an exemplary dose distribution of an optimized plan with two targets located about 4 mm away from each other, according to an embodiment of the present invention.

FIG. 13 illustrates an exemplary dose distribution of an optimized plan with two targets located about 4 mm away from each other. As can be seen, the dose bridging has been successfully limited to 75% of the prescribed dose.

Figure 14:
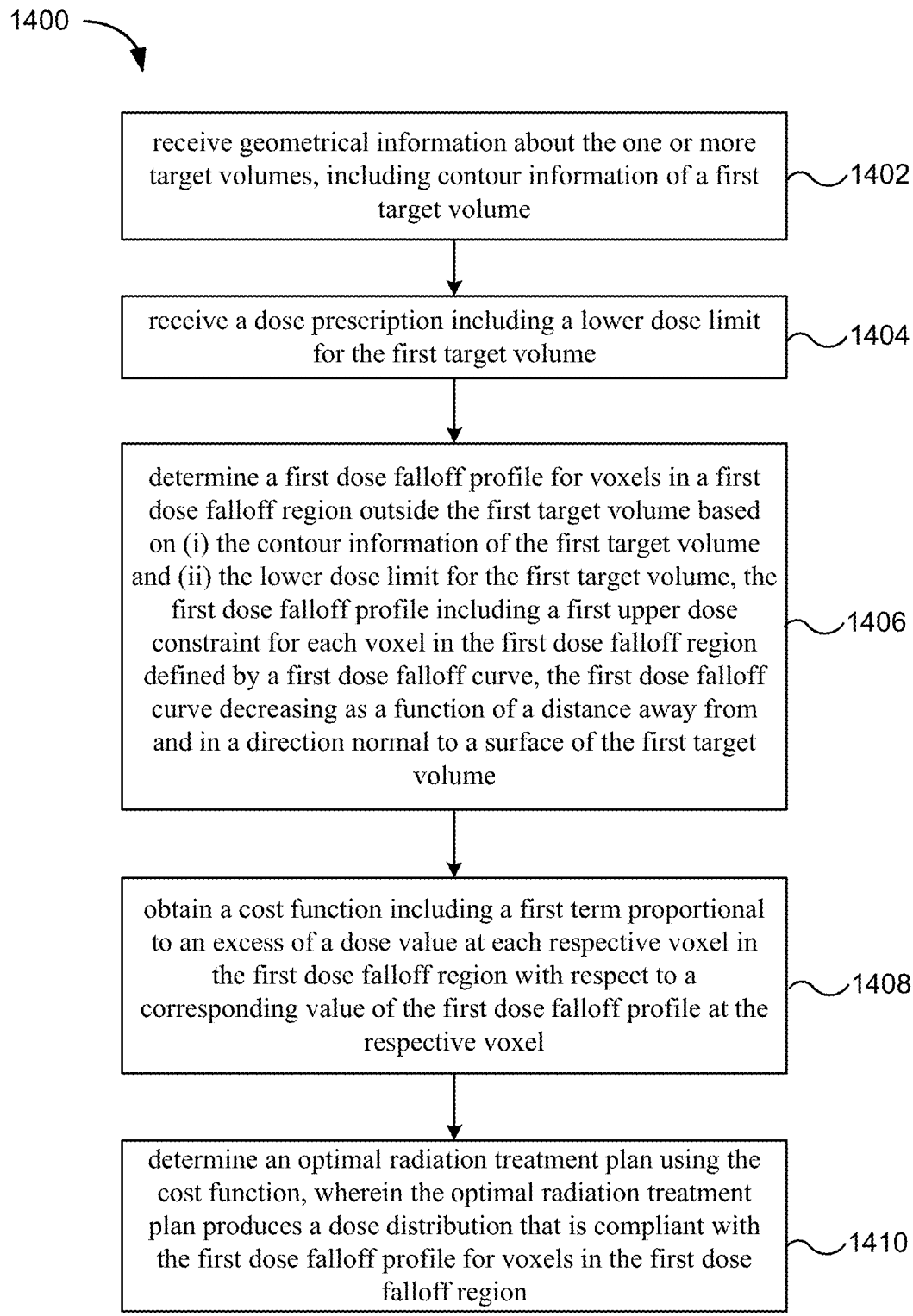
FIG. 14 is a simplified flowchart of a method of controlling the dose distribution outside one or more treatment target volumes within a patient in a radiation treatment plan according to an embodiment of the present invention.

5. Methods of Controlling the Dose Distribution Outside Treatment Target Volumes FIG. 14 is a simplified flowchart of a method 1400 of controlling dose distribution outside one or more treatment target volumes within a domain of interest of a patient in a radiation treatment plan for delivering radiation to the one or more treatment targets using an external-beam radiation treatment system, according to an embodiment of the present invention. Method 1400 can be performed wholly or partially with a computer system, as can other method described herein.

At 1402, geometrical information about the one or more target volumes within the domain of interest of the patient is received. In one embodiment, the one or more target volumes includes a first target volume, and the geometrical information includes contour information of the first target volume.

At 1404, a dose prescription for the one or more target volumes is received. In one embodiment, the dose prescription includes a lower dose limit for the first target volume. In some embodiments, the dose prescription may also include an upper dose limit for the first target volume.

At 1406, a first dose falloff constraint profile for voxels outside the first target volume is determined. In one embodiment, the first dose falloff constraint profile may be determined based on (i) the contour information of the first target volume and (ii) the lower dose limit for the first target volume. In other embodiments, the first dose falloff constraint profile may be determined based on (i) the contour information of the first target volume, (ii) the lower dose limit and the upper dose limit for the first target volume. The first dose falloff constraint profile can include a first upper dose constraint for each voxel outside the first target volume defined by a first dose falloff constraint curve. In some embodiments, the first dose falloff constraint curve decays substantially exponentially as a function of the distance away from and in the direction normal to the surface of the first target volume. In some embodiments, the first dose falloff constraint curve asymptotically decays to a predetermined percentage of the lower dose limit for the first target volume for distances far away from the surface of the first target volume.

At 1408, a cost function is obtained. The cost function can include a first term that is proportional to an excess of a dose value at each respective voxel outside the first target volume with respect to a corresponding value of the first dose falloff constraint profile at the respective voxel. In some embodiments, the first term of the cost function is proportional to square of the excess of the dose value at each respective voxel outside the first target volume with respect to the corresponding value of the first dose falloff constraint profile at the respective voxel.

At 1410, an optimal radiation treatment plan is determined using the cost function. The optimal radiation treatment plan can produce a dose distribution that is compliant with the first dose falloff constraint profile for voxels outside the first target volume. The optimal radiation treatment plan can include a control-point sequence and a multileaf collimator (MLC) leaf sequence to be used by the external-beam radiation treatment system for delivering the radiation.

In some embodiments, the optimal radiation treatment plan is determined by: identifying a plurality of candidate radiation treatment plans, each candidate radiation treatment plan having a respective control-point sequence and a respective multileaf collimator (MLC) leaf sequence for delivering the radiation using the external-beam radiation treatment system; for each of the plurality of candidate radiation treatment plans, determining a corresponding dose distribution for voxels outside the first target volume, and determining a value of the first term of the cost function based on the corresponding dose distribution and the first dose falloff constraint profile; and selecting the optimal radiation treatment plan among the plurality of candidate radiation treatment plans that minimizes the cost function.

In some embodiments, the method 1400 can further includes transmitting the optimal radiation treatment plan to control circuitry of the external-beam radiation treatment system to cause the external-beam radiation treatment system to deliver the radiation to the one or more treatment targets according to the control-point sequence and the multileaf collimator (MLC) leaf sequence of the optimal radiation treatment plan.

In some embodiments, the one or more target volumes can include a second target volume; the geometrical information about the one or more target volumes can include contour information of the second target volume; and the dose prescription can include a lower dose limit for the second target volume. The method 1400 can further include determining a second dose falloff constraint profile for voxels outside the second target volume based on (i) the contour information of the second target volume and (ii) the lower dose limit for the second target volume. In one embodiment, the second dose falloff constraint profile can include a second upper dose constraint for each voxel outside the second target volume defined by a second dose falloff constraint curve. In one embodiment, the first term of the cost function can also be proportional to an excess of a dose value at each respective voxel outside the second target volume with respect to a corresponding value of the second dose falloff constraint profile at the respective voxel.

In some embodiments, each of the first dose falloff constraint curve and the second dose falloff constraint curve can asymptotically decay to a predetermined percentage of a greater of: (i) the lower dose limit for the first target volume and (ii) the lower dose limit for the second target volume, for distances far away from the surface of the first target volume and the surface of the second target volume.

In some embodiments, for each respective voxel in a region outside the first target volume and the second target volume, the first term of the cost function can be proportional to the excess of the dose value at the respective voxel with respect to a greater of: (i) a corresponding value of the first dose falloff constraint profile at the respective voxel, and (ii) a corresponding value of the second dose falloff constraint profile at the respective voxel.

In some embodiments, the method 1400 can further include determining a first dose falloff constraint envelope for voxels outside the first target volume. The first dose falloff constraint envelope can include a third upper dose constraint for each voxel outside the first target volume defined by a third dose falloff constraint curve. In some embodiments, a value of the third dose falloff constraint curve at each respective voxel outside the first target volume is greater than a corresponding value of the first dose falloff constraint curve at the respective voxel. In one embodiment, a value of the third dose falloff constraint curve at each respective voxel outside the first target volume can be equal to a corresponding value of the first dose falloff constraint curve at the respective voxel plus a first positive constant value.

In some embodiments the method 1400 can further include determining a second dose falloff constraint envelope for voxels outside the second target volume. The second dose falloff constraint envelope can include a fourth upper dose constraint for each voxel outside the second target volume defined by a fourth dose falloff constraint curve. In some embodiments, a value of the fourth dose falloff constraint curve at each respective voxel outside the second target volume is greater than a corresponding value of the second dose falloff constraint curve at the respective voxel. In one embodiment, a value of the fourth dose falloff constraint curve at each respective voxel outside the second target volume can be equal to a corresponding value of the second dose falloff constraint curve plus a second positive constant value.

In some embodiments, each of the third dose falloff constraint curve and the fourth dose falloff constraint curve can asymptotically decay to a predetermined percentage of a greater of: (i) the lower dose limit for the first target volume, and (ii) the lower dose limit for the second target volume, for distances far away from the surface of the first target volume and the surface of the second target volume. In one embodiment, the predetermined percentage can depend on a shortest distance between the surface of the first target volume and the surface of the second target volume.

In some embodiments, the cost function can further include a second term. For each respective voxel outside the first target volume and the second target volume, the second term can be proportional to an excess of a dose value at the respective voxel with respect to a greater of: (i) a corresponding value of the first dose falloff constraint envelope at the respective voxel, and (ii) a corresponding value of the second dose falloff constraint envelope at the respective voxel. In some embodiments, the optimal radiation treatment plan can produce a dose distribution for voxels outside the first target volume and the second target volume that is compliant with the first dose falloff constraint envelope and the second dose falloff constraint envelope. In some embodiments, the second term of the cost function can be proportional to square of the excess of the dose value at the respective voxel with respect to the greater of: (i) the corresponding value of the first dose falloff constraint envelope at the respective voxel, and (ii) the corresponding value of the second dose falloff constraint envelope at the respective voxel. In one embodiment, the first term of the cost function has a first weight, and the second term of the cost function has a second weight greater than the first weight.

In some embodiments, the cost function can further include a third term for voxels in an intermediate region about mid-way between the surface of the first target volume and the surface of the second target volume. For each respective voxel in the intermediate region, the third term can be proportional to an excess of a dose value at the respective voxel with respect to a predetermined percentage of a greater of: (i) the lower dose limit for the first target volume, and (ii) the lower dose limit for the second target volume.

It should be appreciated that the specific steps illustrated in FIG. 14 provide a particular method according to an embodiment of the present invention. For the method, other sequences of steps may also be performed according to alternative embodiments. For example, alternative embodiments of the present invention may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

IV. Computer System

Figure 15:
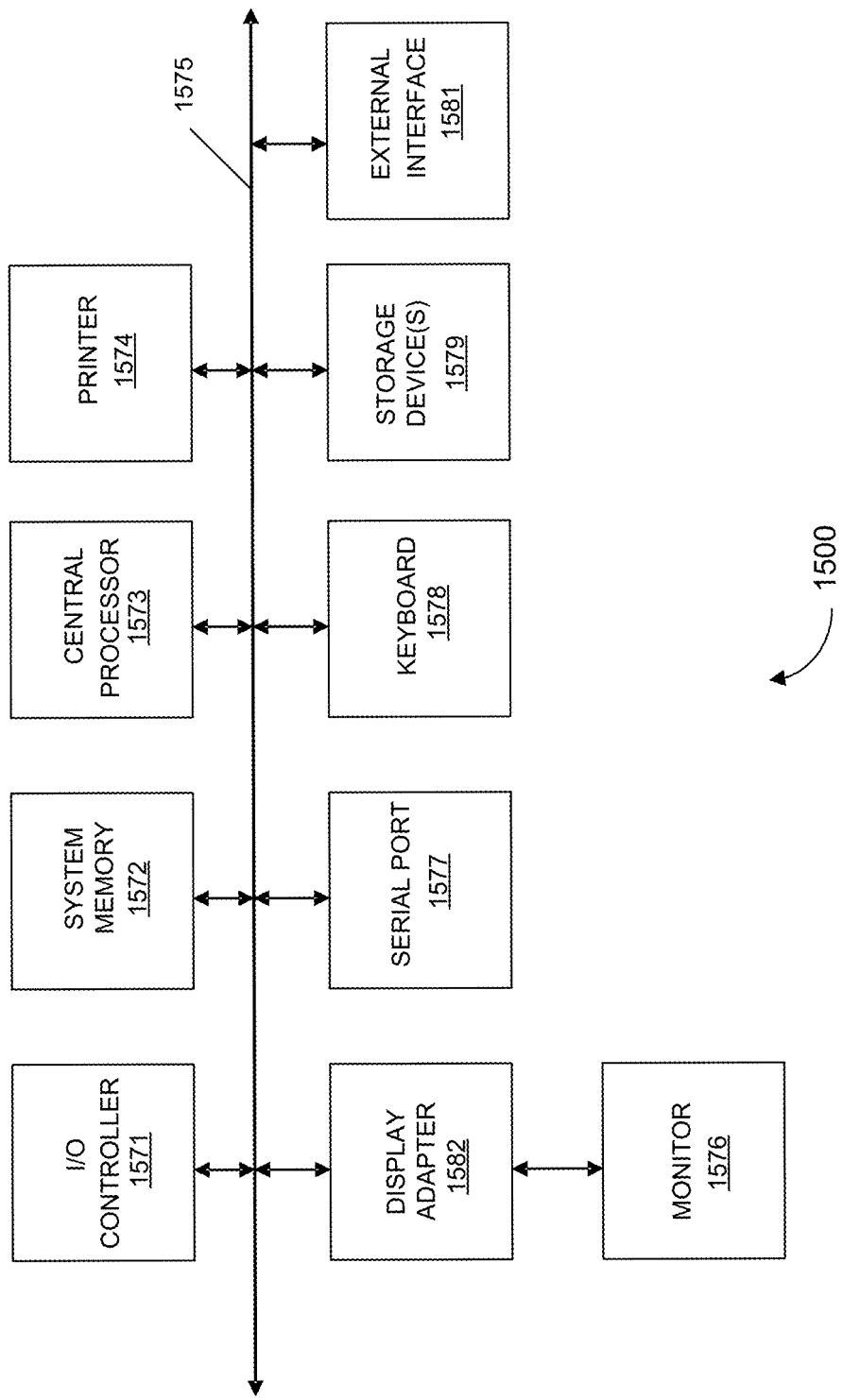
FIG. 15 shows a block diagram of an example computer system usable with system and methods according to embodiments of the present invention.

Any of the computer systems mentioned herein may utilize any suitable number of subsystems. Examples of such subsystems are shown in FIG. 15 in computer system 1500. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 15 are interconnected via a system bus 1575. Additional subsystems such as a printer 1574, keyboard 1578, storage device(s) 1579, monitor 1576, which is coupled to display adapter 1582, and others are shown. Peripherals and input/output (I/O) devices, which couple to I/O controller 1571, can be connected to the computer system by any number of means known in the art, such as serial port 1577. For example, serial port 1577 or external interface 1581 (e.g. Ethernet, Wi-Fi, etc.) can be used to connect computer system 1500 to a wide area network such as the Internet, a mouse input device, or a scanner. The interconnection via system bus 1575 allows the central processor 1573 to communicate with each subsystem and to control the execution of instructions from system memory 1572 or the storage device(s) 1579 (e.g., a fixed disk, such as a hard drive or optical disk), as well as the exchange of information between subsystems. The system memory 1572 and/or the storage device(s) 1579 may embody a computer readable medium. Any of the data mentioned herein can be output from one component to another component and can be output to the user.

A computer system can include a plurality of the same components or subsystems, e.g., connected together by external interface 1581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A computer product comprising a non-transitory computer readable medium storing a plurality of instructions that when executed control a computer system to determine a radiation treatment plan for irradiating one or more target volumes within a domain of interest of a patient using an external-beam radiation treatment system, the instructions comprising:
   receiving geometrical information about the one or more target volumes, wherein the one or more target volumes include a first target volume, and wherein the geometrical information includes contour information of the first target volume;
   receiving a dose prescription including a lower dose limit for the first target volume;
   determining a first dose falloff constraint profile for voxels outside the first target volume based on (i) the contour information of the first target volume and (ii) the lower dose limit for the first target volume, wherein the first dose falloff constraint profile includes a first upper dose constraint for each voxel outside the first target volume defined by a first dose falloff constraint curve;
   obtaining a cost function including a first term proportional to an excess of a dose value at each respective voxel outside the first target volume with respect to a corresponding value of the first dose falloff constraint profile at the respective voxel; and
   determining an optimal radiation treatment plan using the cost function, wherein the optimal radiation treatment plan produces a dose distribution that is compliant with the first dose falloff constraint profile for voxels outside the first target volume.

2. The computer product of claim 1, wherein determining the optimal radiation treatment plan comprises:
   identifying a plurality of candidate radiation treatment plans, each candidate radiation treatment plan having a respective control-point sequence and a respective multileaf collimator (MLC) leaf sequence for delivering radiation using the external-beam radiation treatment system;
   for each of the plurality of candidate radiation treatment plans:
      determining a corresponding dose distribution for voxels outside the first target volume; and
      determining a value of the first term of the cost function based on the corresponding dose distribution and the first dose falloff constraint profile; and selecting the optimal radiation treatment plan among the plurality of candidate radiation treatment plans that minimizes the cost function.

3. The computer product of claim 1, wherein the optimal radiation treatment plan includes a control-point sequence and a multileaf collimator (MLC) leaf sequence to be used by the external-beam radiation treatment system for delivering radiation to the patient.

4. The computer product of claim 3, wherein the instructions further comprise transmitting the optimal radiation treatment plan to control circuitry of the external-beam radiation treatment system to cause the external-beam radiation treatment system to deliver radiation to the one or more target volumes according to the control-point sequence and the multileaf collimator (MLC) leaf sequence of the optimal radiation treatment plan.

5. The computer product of claim 1, wherein the first term of the cost function is proportional to square of the excess of the dose value at each respective voxel outside the first target volume with respect to the corresponding value of the first dose falloff constraint profile at the respective voxel.

6. The computer product of claim 1, wherein the first dose falloff constraint curve decays substantially exponentially as a function of a distance away from and in a direction normal to a surface of the first target volume.

7. The computer product of claim 6, wherein the first dose falloff constraint curve decays asymptotically to a predetermined percentage of the lower dose limit for the first target volume for distances far away from the surface of the first target volume.

8. The computer product of claim 1, wherein:
the dose prescription further includes an upper dose limit for the first target volume; and
determining the first dose falloff constraint profile is based on both the lower dose limit and the upper dose limit for the first target volume.

9. The computer product of claim 1, wherein:
the one or more target volumes further includes a second target volume;
the geometrical information about the one or more target volumes further includes contour information of the second target volume;
the dose prescription further includes a lower dose limit for the second target volume; and
the instructions further comprising:
determining a second dose falloff constraint profile for voxels outside the second target volume based on (i) the contour information of the second target volume and (ii) the lower dose limit for the second target volume, wherein the second dose falloff constraint profile includes a second upper dose constraint for each voxel outside the second target volume defined by a second dose falloff constraint curve;
wherein the first term of the cost function is further proportional to an excess of a dose value at each respective voxel outside the second target volume with respect to a corresponding value of the second dose falloff constraint profile at the respective voxel.

10. The computer product of claim 9, wherein each of the first dose falloff constraint curve and the second dose falloff constraint curve asymptotically decays to a predetermined percentage of a greater of: (i) the lower dose limit for the first target volume and (ii) the lower dose limit for the second target volume, for distances far away from a surface of the first target volume and a surface of the second target volume.

11. The computer product of claim 9, wherein, for each respective voxel in a region outside the first target volume and the second target volume, the first term of the cost function is proportional to the excess of the dose value at the respective voxel with respect to a greater of: (i) a corresponding value of the first dose falloff constraint profile at the respective voxel, and (ii) a corresponding value of the second dose falloff constraint profile at the respective voxel.

12. The computer product of claim 11, wherein the instructions further comprise:
determining a first dose falloff constraint envelope for voxels outside the first target volume, wherein the first dose falloff constraint envelope includes a third upper dose constraint for each voxel outside the first target volume defined by a third dose falloff constraint curve; and
determining a second dose falloff constraint envelope for voxels outside the second target volume, wherein the second dose falloff constraint envelope includes a fourth upper dose constraint for each voxel outside the second target volume defined by a fourth dose falloff constraint curve;
wherein the cost function further includes a second term, and wherein for each respective voxel in a region outside the first target volume and the second target volume, the second term is proportional to an excess of a dose value at the respective voxel with respect to a greater of: (i) a corresponding value of the first dose falloff constraint envelope at the respective voxel, and (ii) a corresponding value of the second dose falloff constraint envelope at the respective voxel; and
wherein the optimal radiation treatment plan produces a dose distribution for voxels in an overlap region that is compliant with the first dose falloff constraint envelope and the second dose falloff constraint envelope.

13. The computer product of claim 12, wherein the second term of the cost function is proportional to square of the excess of the dose value at the respective voxel with respect to the greater of: (i) the corresponding value of the first dose falloff constraint envelope at the respective voxel, and (ii) the corresponding value of the second dose falloff constraint envelope at the respective voxel.

14. The computer product of claim 12, wherein the first term of the cost function has a first weight, and the second term of the cost function has a second weight greater than the first weight.

15. The computer product of claim 12, wherein:
a value of the third dose falloff constraint curve at each respective voxel outside the first target volume is greater than a corresponding value of the first dose falloff constraint curve at the respective voxel; and
a value of the fourth dose falloff constraint curve at each respective voxel outside the second target volume is greater than a corresponding value of the second dose falloff constraint curve at the respective voxel.

16. The computer product of claim 15, wherein:
a value of the third dose falloff constraint curve at each respective voxel outside the first target volume is equal to a corresponding value of the first dose falloff constraint curve at the respective voxel in a first dose falloff region plus a first positive constant value; and
a value of the fourth dose falloff constraint curve at each respective voxel outside the second target volume is equal to a corresponding value of the second dose falloff constraint curve at the respective voxel in a second dose falloff region plus a second positive constant value.

17. The computer product of claim 12, wherein:
each of the third dose falloff constraint curve and the fourth dose falloff constraint curve asymptotically decays to a predetermined percentage of a greater of: (i) the lower dose limit for the first target volume, and (ii) the lower dose limit for the second target volume.

18. The computer product of claim 17, wherein the predetermined percentage depends on a shortest distance between a surface of the first target volume and a surface of the second target volume.

19. The computer product of claim 12, wherein the cost function further includes a third term for voxels in an intermediate region about mid-way between a surface of the first target volume and a surface of the second target volume, and wherein for each respective voxel in the intermediate region, the third term is proportional to an excess of a dose value at the respective voxel with respect to a predetermined percentage of a greater of: (i) the lower dose limit for the first target volume, and (ii) the lower dose limit for the second target volume.

20. A radiation therapy system comprising:
a radiation therapy device including:
  a rotatable gantry including a treatment head and a multileaf collimator, wherein the multileaf collimator is configured to shape a radiation beam emitted from the treatment head; and
  a control unit configured to:
    control a rotation of the rotatable gantry;
    control emission of the radiation beam from the treatment head; and
    control a shape of the radiation beam via the multileaf collimator;
  one or more processors; and
  a non-transitory computer readable medium storing a plurality of instructions that when executed control the one or more processors to determine a radiation treatment plan for irradiating one or more target volumes within a domain of interest of a patient using the radiation therapy device, the instructions comprising:
    receiving geometrical information about the one or more target volumes, wherein the one or more target volumes include a first target volume, and wherein the geometrical information includes contour information of the first target volume;
    receiving a dose prescription including a lower dose limit for the first target volume;
    determining a first dose falloff constraint profile for voxels outside the first target volume based on (i) the contour information of the first target volume and (ii) the lower dose limit for the first target volume, wherein the first dose falloff constraint profile includes a first upper dose constraint for each voxel outside the first target volume defined by a first dose falloff constraint curve;
    obtaining a cost function including a first term proportional to an excess of a dose value at each respective voxel outside the first target volume with respect to a corresponding value of the first dose falloff constraint profile at the respective voxel; and
    determining an optimal radiation treatment plan using the cost function, wherein the optimal radiation treatment plan produces a dose distribution that is compliant with the first dose falloff constraint profile for voxels outside the first target volume.

* * * * *